United States Patent [19]
Cohen

[11] Patent Number: 5,462,069
[45] Date of Patent: Oct. 31, 1995

[54] POST-SURGICAL TOE GUARD AND TONGUE

[76] Inventor: Jack Cohen, 811 Avenue S, Brooklyn, N.Y. 11223

[21] Appl. No.: 272,901

[22] Filed: Jul. 8, 1994

Related U.S. Application Data

[63] Continuation of Ser. No. 956,178, Oct. 5, 1992, abandoned.

[51] Int. Cl.[6] ........................... A61F 13/06; A61F 5/00
[52] U.S. Cl. ............................... 128/893; 602/30
[58] Field of Search .................... 128/893, 894, 128/882; 602/30, 11; 36/7.2; 2/239

[56] References Cited

U.S. PATENT DOCUMENTS

| | | | |
|---|---|---|---|
| 840,717 | 1/1907 | Schultz | 128/894 |
| 1,175,718 | 3/1916 | Crowe | 128/894 |
| 2,244,844 | 6/1941 | Margel | 128/894 |
| 2,335,665 | 11/1943 | Goldmerstein | 128/894 |
| 2,792,001 | 5/1957 | Ryan | 128/893 |
| 2,958,324 | 11/1960 | Berkemann | 602/30 |
| 3,049,120 | 8/1962 | Marus | 602/30 |
| 3,050,057 | 8/1962 | Johnson | 128/893 |
| 3,299,894 | 1/1967 | Charlebois | 602/30 |
| 3,334,356 | 8/1967 | Abel | 128/894 |
| 3,487,830 | 1/1970 | Pruett | 602/11 |
| 3,834,377 | 9/1974 | Lebold | 128/DIG. 15 |
| 4,069,599 | 1/1978 | Alegria | 36/7.2 |
| 4,078,266 | 3/1978 | Brown | 602/30 |
| 4,237,628 | 12/1980 | Etancelin | 36/7.2 |
| 4,495,715 | 1/1985 | Fredrickson | 36/7.2 |
| 4,729,369 | 3/1988 | Cook | 602/30 |

FOREIGN PATENT DOCUMENTS

| | | | |
|---|---|---|---|
| 0545026 | 8/1957 | Canada | 128/893 |
| 0019607 | of 1903 | United Kingdom | 128/893 |
| 0232035 | 4/1925 | United Kingdom | 128/893 |

*Primary Examiner*—Michael A. Brown
*Attorney, Agent, or Firm*—Ezra Sutton

[57] ABSTRACT

A device to be used with a post-surgical boot for protecting the toes from injury and uncleanliness, which includes a base section, a toe-covering section, and an integral tongue section.

18 Claims, 2 Drawing Sheets

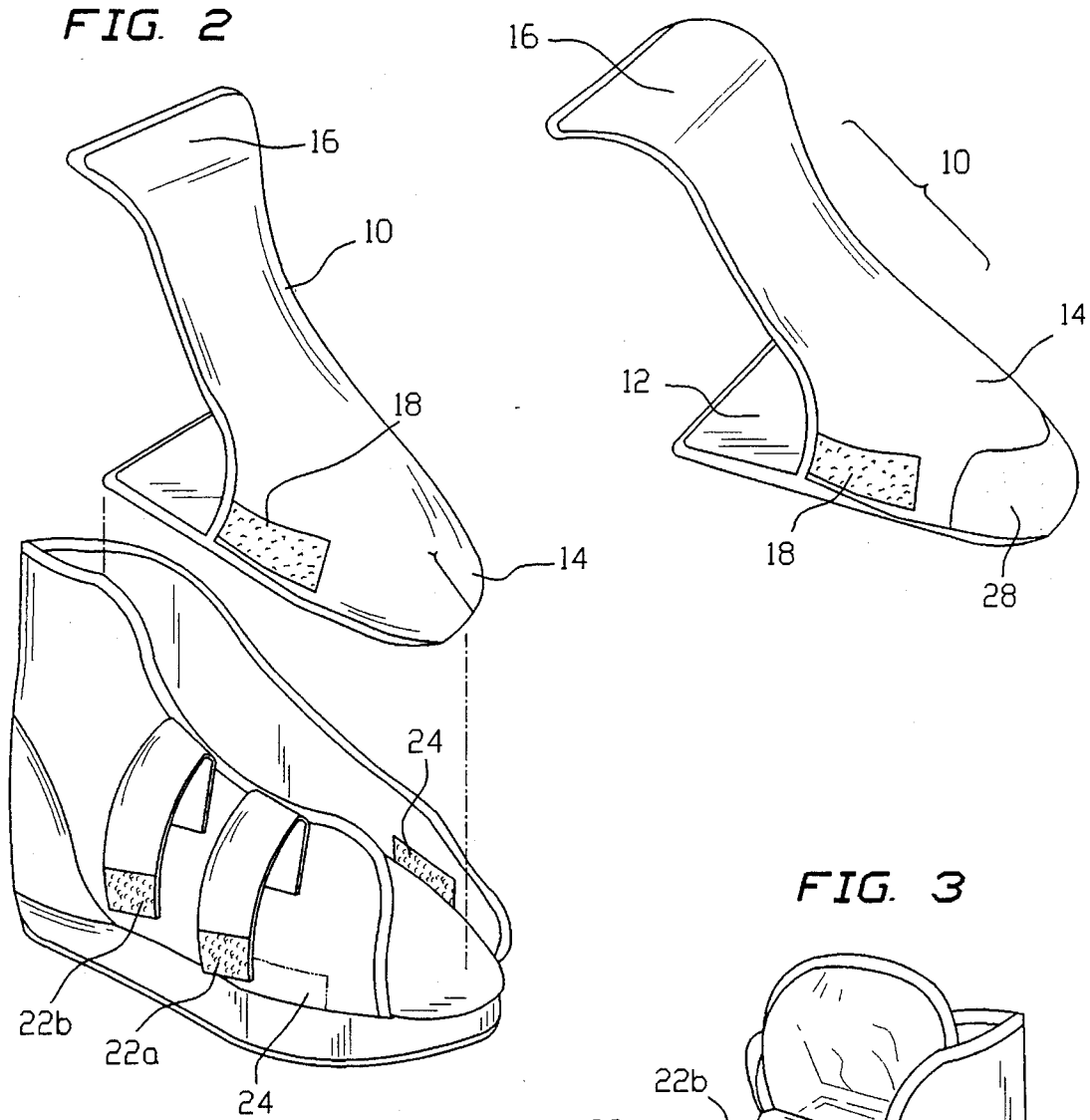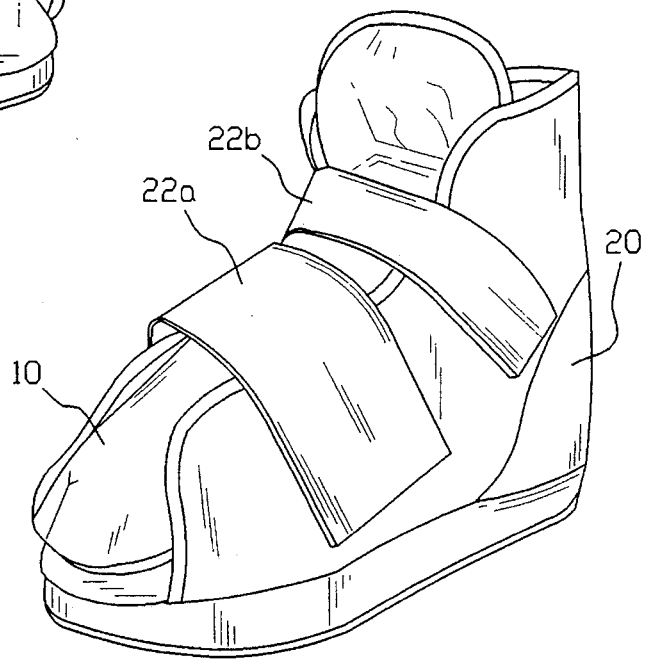

POST-SURGICAL TOE GUARD AND TONGUE

This application is a continuation of application Ser. No. 07/956,178, filed Oct. 5, 1992, now abandoned.

FIELD OF THE INVENTION

The present invention relates to a toe guard to be used within a post-surgical boot or shoe subsequent to surgical procedures on the foot.

BACKGROUND OF THE INVENTION

After patients undergo surgical procedures on the foot, they usually must wear some type of post-surgical boot or shoe around the effected area to provide support, rigidity, and protection. However, the prior art does not provide a toe guard for inserting inside a post-surgical boot or shoe which will cover the toes and protect them from uncleanliness and injury, and provide the require support.

U.S. Pat. No. 3,487,830 provides a post-surgical toe guard, but this design is not intended to be worn inside a shoe, and it is solely for external use. The design is made for contact with the ground, as in walking, and is used in cooperation with a heel from a cast to replace a shoe. Additionally, the design lacks a tongue providing only limited protection to the patient.

It is an object of the present invention to provide a toe guard that may be worn inside of any post-surgical boot or protective shoe.

It is a further object of the present invention to provide the toe guard with an integral tongue member to provide additional comfort and protection to the wearer.

SUMMARY OF THE INVENTION

In accordance with the principles of the present invention, there is provided a surgical toe guard to be worn inside a surgical boot or shoe. This toe guard will protect the toes from uncleanliness and injury, and provide the necessary support.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein:

FIG. 2 shows how the surgical toe guard is insertable and attachable to present surgical boot designs;

FIG. 3 is an illustration of the toe guard in use with a surgical boot as the invention would be worn by a patient;

FIG. 5 is a perspective view of the invention showing a safety section to protect the toes.

DETAILED DESCRIPTION OF THE PREFERRED EMBODIMENTS

Figure 1:
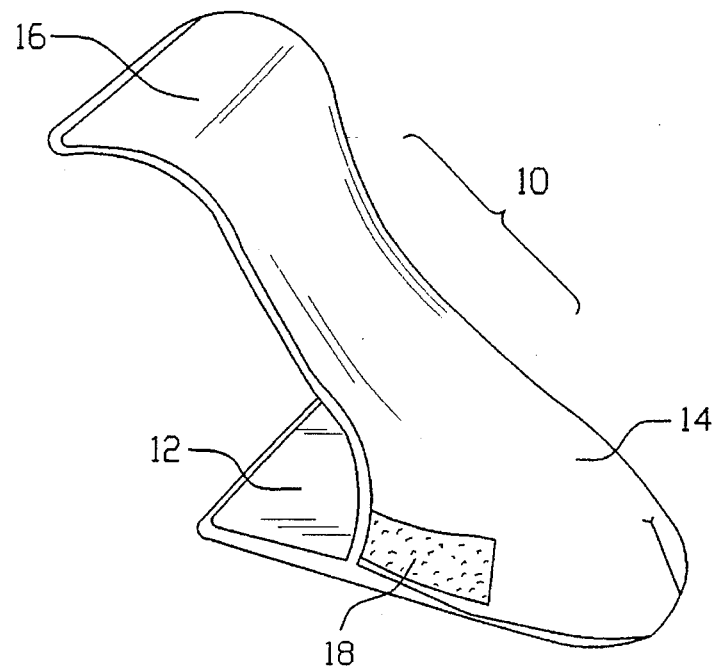
FIG. 1 is a perspective view of the surgical toe guard of the present invention.

Referring to FIG. 1, there is shown a post-surgical toe guard 10 embodying the principles of the present invention. The post-surgical toe guard 10 comprises a base section 12 connected to a toe-covering section 14 and an integrally-formed tongue section 16, all cooperating to form a toe-receiving compartment 30. An attachment device 18 is located on the exterior of toe-covering section 14 to secure the toe guard 10 to the inside of a surgical boot 20.

The post-surgical toe guard 10 is made of leather, cloth, PVC, canvas, or fabric material to provide comfort to the patient during use. The foot of the patient is placed in the toe-receiving compartment 30 of the toe guard 10. The foot is supported by a base section 12 beneath the foot and is protected above by the toe-covering section 14 and the integrally-formed tongue section 16. In addition, the tongue section 16 provides comfort to the upper foot by preventing irritation to the foot from straps 22 on the post-surgical boot 20, as seen in FIG. 3. Preferably, the tongue section is about 3 inches in length, but the size may vary. The attachment device 18 is located on the exterior of the toe-covering section 14 to secure the toe guard 10 to the inside of a post-surgical boot 20. The attachment device 18 is a fastener which may include one or a plurality of Velcro strips, buckles, buttons, zippers, straps, strings, or snap fasteners.

Referring to FIGS. 1, 2, and 3, there is shown a post-surgical toe guard 10 in use with a post-surgical boot 20. The toe guard 10 is inserted into the surgical boot 20 and held in place by the attachment device 18, located on the exterior surface of the toe-covering section 14 of the toe guard 10. The attachment device 18 secures the toe guard 10 to the interior surface 24 of the post-surgical boot 20. The toe guard 10 is further secured in place by a plurality of Velcro straps 22a and 22b located on the post-surgical boot 20. FIG. 3 illustrates how the present invention would appear as worn by a patient.

Figure 4:
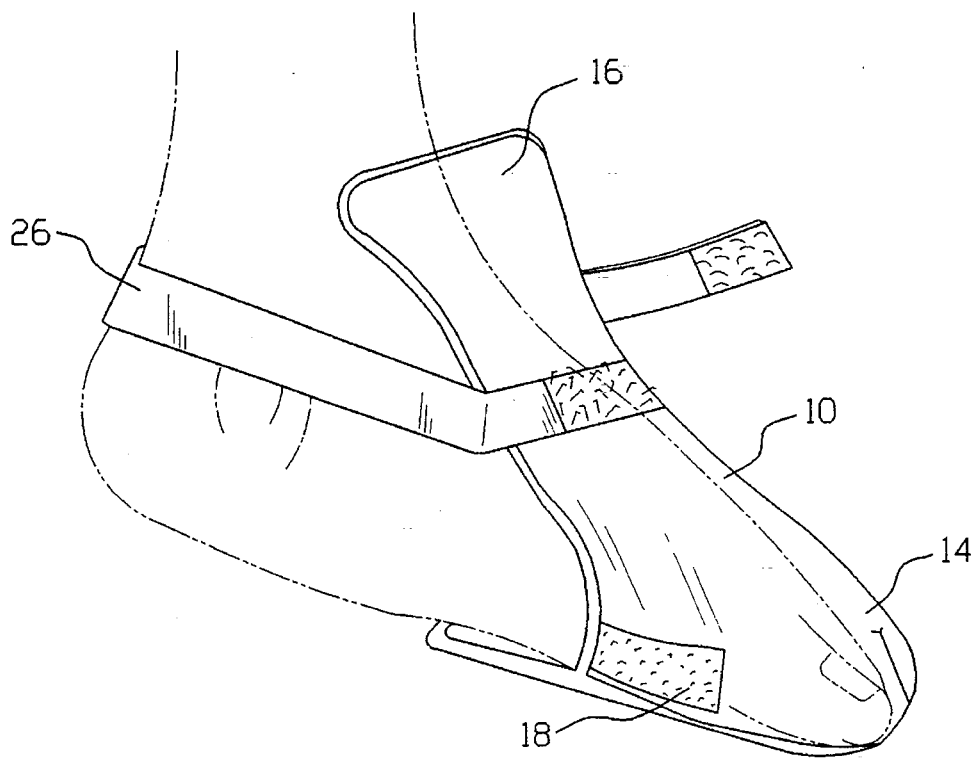
FIG. 4 is an alternative embodiment of the present invention showing a sling for securing the toe guard to the ankle.

Referring to FIG. 4, there is shown an alternative embodiment of the present invention. The toe guard 10 is provided with an adjustable and stretchable strap 26 to secure the toe guard 10 to the ankle or heel of the patient. The strap 26 prevents the toe guard 10 from moving or sliding while being worn.

FIG. 5 illustrates a surgical toe guard 10 with an additional safety section or cup 28 located at the toe-covering section 14. The safety section 28 is made of rigid plastic, metal, or similar rigid material which protects the toes from injury. The safety section 28 is removable from the toe guard 10, if desired.

Advantageously, the present invention provides an improved toe guard and protector, which insures cleanliness, comfort, and safety for the patient.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A post-surgical toe guard and integral tongue member to be worn inside a post-surgical boot or shoe, comprising:
   a) a base section;
   b) a one-compartment toe-covering section for covering all of the toes of the wearer in said one compartment, said toe-covering section connected to said base section to form a toe-receiving guard;
   c) a tongue section integrally connected to said toe-covering guard and extending from said toe-covering section along the top surface of the upper foot; and
   d) means on the exterior surface of said toe-covering guard for attaching said toe guard to the interior surface of a post-surgical shoe or boot.

2. A post-surgical toe guard in accordance with claim 1, wherein said means for attaching to the interior surface of a post-surgical shoe or boot is a hook and loop fastener.

3. A post-surgical toe guard in accordance with claim 1, wherein said means for attaching to a post-surgical shoe are snap fasteners, buckles, buttons, zippers, straps, strings, or other fastening means.

4. A post-surgical toe guard in accordance with claim 1, wherein said toe guard is made of cloth or woven fabric material.

5. A post-surgical toe guard in accordance with claim 1, wherein said toe guard is made of leather or similar material.

6. A post-surgical toe guard in accordance with claim 1, wherein said toe guard includes means for securing said toe guard to the heel, ankle, or leg of the wearer.

7. A post-surgical toe guard in accordance with claim 6, wherein said means for securing said toe guard is an adjustable and stretchable strap, string, belt, or similar device.

8. A post-surgical toe guard in accordance with claim 1, wherein said toe-covering section includes a rigid safety section to protect the toes from injury.

9. A post-surgical toe guard in accordance with claim 8, wherein said safety section is a cup made of a plastic, metal, or other rigid material.

10. A post-surgical toe guard in accordance with claim 8, wherein said safety section is removable from the inside of said toe-receiving compartment.

11. A post-surgical toe guard in accordance with claim 10, wherein said toe-covering section includes a rigid safety section to protect the toes from injury.

12. A post-surgical toe guard in accordance with claim 11, wherein said safety section is a cup made of a plastic, metal, or other rigid material.

13. A post-surgical toe guard in accordance with claim 11, wherein said safety section is removable from the inside of said toe-receiving compartment.

14. A post-surgical toe guard to be worn inside a post-surgical boot or shoe, comprising:
  a) a base section;
  b) a one-compartment toe-covering section for covering all of the toes of the wearer in said one compartment, said toe-covering section connected to said base section to form a toe-receiving guard; and
  c) means on the exterior surface of said toe-covering guard for attaching said toe guard to the interior surface of a post-surgical shoe or boot.

15. A post-surgical toe guard in accordance with claim 14, wherein said means for attaching to the interior surface of a post-surgical shoe or boot is a hook and loop fastener.

16. A post-surgical toe guard in accordance with claim 14, wherein said toe guard is made of cloth or woven fabric material.

17. A post-surgical toe guard in accordance with claim 14, wherein said toe guard includes means for securing said toe guard to the heel, ankle, or leg of the wearer.

18. A post-surgical toe guard in accordance with claim 17, wherein said means for securing said toe guard is an adjustable and stretchable strap, string, belt, or similar device.

* * * * *